United States Patent
Hultgren

(10) Patent No.: US 8,821,158 B1
(45) Date of Patent: Sep. 2, 2014

(54) METHOD AND APPARATUS FOR MATCHING DIGITAL THREE-DIMENSIONAL DENTAL MODELS WITH DIGITAL THREE-DIMENSIONAL CRANIO-FACIAL CAT SCAN RECORDS

(75) Inventor: Bruce Willard Hultgren, Victoria, MN (US)

(73) Assignee: GeoDigm Corporation, Chanhassen, MN (US)

(*) Notice: Subject to any disclaimer, the term of this patent is extended or adjusted under 35 U.S.C. 154(b) by 2034 days.

(21) Appl. No.: 09/689,137

(22) Filed: Oct. 12, 2000

Related U.S. Application Data

(60) Provisional application No. 60/159,304, filed on Oct. 14, 1999.

(51) Int. Cl.
    *A61C 3/00* (2006.01)
(52) U.S. Cl.
    USPC ............. 433/29; 433/24; 433/72; 433/215
(58) Field of Classification Search
    USPC ........... 433/6, 24, 29, 37, 72, 215; 378/163, 378/162, 168, 170; 600/1, 3, 7
    See application file for complete search history.

(56) References Cited

U.S. PATENT DOCUMENTS

| | | | |
|---|---|---|---|
| 4,521,186 A * | 6/1985 | Wodlinger et al. | 433/71 |
| 4,575,805 A | 3/1986 | Moermann et al. | |
| 4,611,288 A | 9/1986 | Duret et al. | |
| 4,734,034 A * | 3/1988 | Maness et al. | 433/71 |
| 4,837,732 A | 6/1989 | Brandestini et al. | |
| 4,856,993 A * | 8/1989 | Maness et al. | 433/71 |
| 5,113,424 A * | 5/1992 | Burdea et al. | 378/170 |
| 5,267,293 A * | 11/1993 | Virta | 378/40 |
| 5,273,429 A | 12/1993 | Rekow et al. | |
| 5,343,391 A | 8/1994 | Mushabac | |
| 5,347,454 A | 9/1994 | Mushabac | |
| 5,368,478 A | 11/1994 | Andreiko et al. | |
| 5,372,502 A | 12/1994 | Massen et al. | |
| 5,395,239 A * | 3/1995 | Komatsu et al. | 433/71 |
| 5,416,822 A * | 5/1995 | Kunik | 378/162 |
| 5,431,562 A | 7/1995 | Andreiko et al. | |
| 5,448,472 A | 9/1995 | Mushabac | |

(Continued)

OTHER PUBLICATIONS

Hayashi, T. et al., "A Computerized System for Analyzing Occlusal Relations During Mandibular Movements," *The Intl. Journal of Prosthodontics*, vol. 7, No. 2, pp. 108-114 (Mar./Apr. 1994).

*Primary Examiner* — Laura Bouchelle
(74) *Attorney, Agent, or Firm* — Merchant & Gould P.C.

(57) ABSTRACT

The system creates digital images of teeth topography using a dental impression tray that provides registration information for integration of a digital three-dimensional model with a digital three-dimensional cranio-facial CAT scan record. The impression tray is held in the patient's mouth during a CAT scan. The tray includes fiduciary markers that can be accurately located by the CAT scan. The tray also includes a dental impression material which, subsequent to the CAT scan, is removed from the patient's mouth and placed on a table of an X-Y-Z scanning machine for scanning the impression. In this manner, a set of electronic data related to the patient's teeth and surrounding soft tissues is generated. The fiduciary markers, which may be constructed of titanium, are included in both sets of electronic data for the patient's teeth. The markers are then used as common reference points in the spatial matching of the two scans.

7 Claims, 17 Drawing Sheets

(56) References Cited

U.S. PATENT DOCUMENTS

| | | |
|---|---|---|
| 5,518,397 A | 5/1996 | Andreiko et al. |
| 5,533,895 A | 7/1996 | Andreiko et al. |
| 5,549,476 A | 8/1996 | Stern |
| 5,569,578 A | 10/1996 | Mushabac |
| 5,588,430 A * | 12/1996 | Bova et al. .......... 128/653.1 |
| 5,605,459 A | 2/1997 | Kuroda et al. |
| 5,879,158 A | 3/1999 | Doyle et al. |
| 6,068,482 A | 5/2000 | Snow |
| 6,123,544 A | 9/2000 | Cleary |
| 6,143,003 A | 11/2000 | Cosman |
| 6,322,359 B1 | 11/2001 | Jordan et al. |
| 6,371,761 B1 | 4/2002 | Cheang et al. |
| 6,409,504 B1 | 6/2002 | Jones et al. |
| 6,450,807 B1 | 9/2002 | Chishti et al. |
| 6,554,613 B1 | 4/2003 | Sachdeva et al. |
| 6,632,089 B2 | 10/2003 | Rubbert et al. |
| 6,648,640 B2 | 11/2003 | Rubbert et al. |
| 6,688,886 B2 | 2/2004 | Hughes et al. |
| 6,905,337 B1 | 6/2005 | Sachdeva |
| 2003/0224316 A1 | 12/2003 | Marshall |
| 2004/0066877 A1 | 4/2004 | Arai et al. |

\* cited by examiner

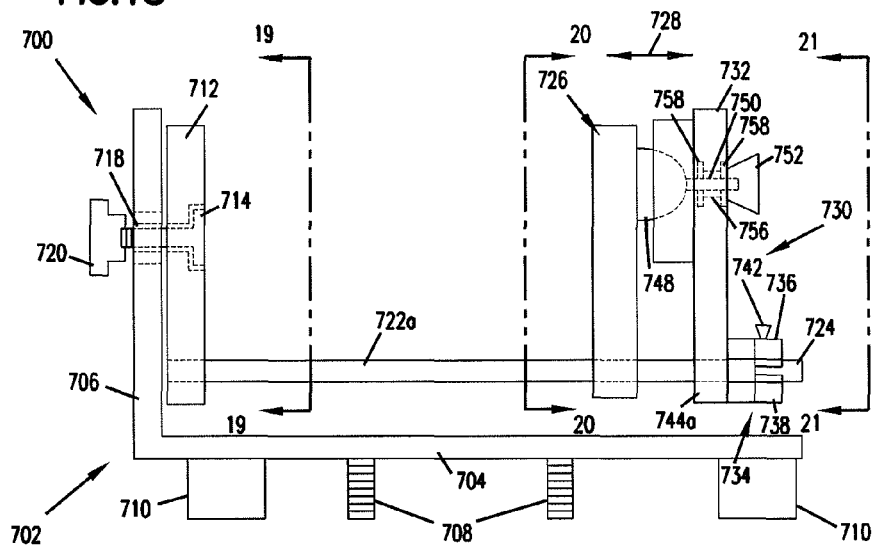

FIG. 24
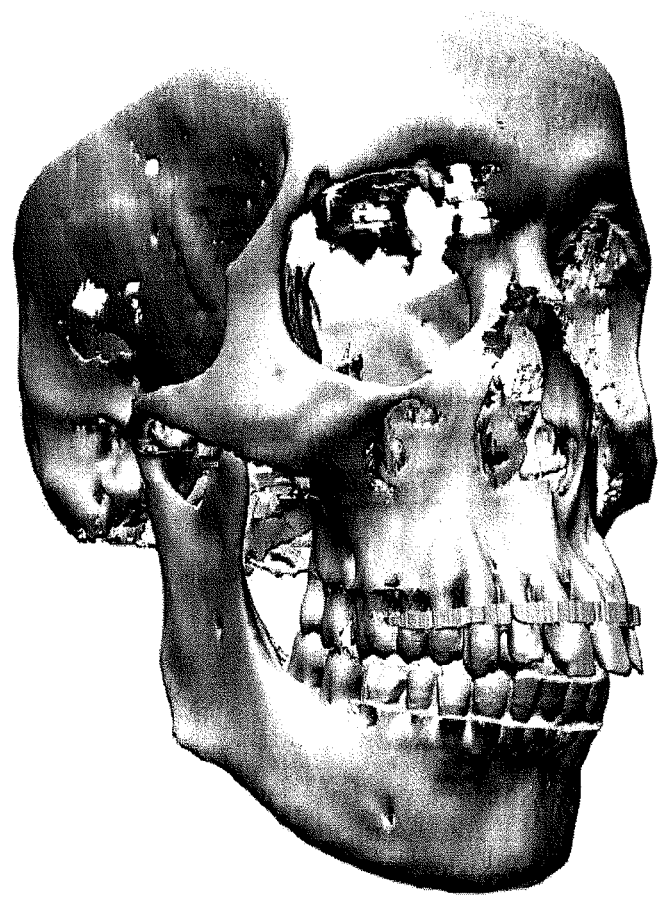
810

METHOD AND APPARATUS FOR MATCHING DIGITAL THREE-DIMENSIONAL DENTAL MODELS WITH DIGITAL THREE-DIMENSIONAL CRANIO-FACIAL CAT SCAN RECORDS

CROSS REFERENCE TO RELATED APPLICATION

This application claims the benefit of U.S. Provisional Application No. 60/159,304 filed Oct. 14, 1999.

FIELD OF THE INVENTION

The present invention relates generally to a system of dental modeling and imaging which creates digital images of teeth topography; and more particularly relates to a dental impression tray which provides registration information for integration of the resulting digital three-dimensional model with a digital three-dimensional cranio-facial CAT scan record.

BACKGROUND

Patients that are undergoing oral surgery will typically be prescribed by their doctor to have a computer aided tomography (CAT scan) record created of the affected cranio-facial region. For example, patients undergoing correction of facial deformities, facial reconstruction after injury, and placement of dental implants often will have such a CAT scan performed.

CAT scan records are basically a series of X-Rays taken a short distance apart along a set path, whereby a three-dimensional presentation of the patient's bone structure, nerves, and facial soft tissue can be generated on a computer screen for aiding the doctor in the determination of the patient's treatment diagnosis.

In the application of oral surgery, the CAT scan record commonly has missing or inaccurate medical information in the region of the teeth biting surfaces. The missing or inaccurate data is caused by the presence of metal dental fillings, or metal dental prostheses (crowns, bridges, etc.) typically present in teeth. When metal is present in or near a patient's teeth, it causes the gamma X-rays to be scattered in that region, producing a "data void" in the oral region of the CAT scan record. For years, efforts have been made to overcome this problem. To date, however, the problem of missing and/or inaccurate medical information in the regions of the biting surfaces has not been eliminated.

Therefore, there arises a need for a method and apparatus which enhances the CAT-scan medical records of those patients considering or undergoing oral surgery. The method and apparatus should provide preferably missing or inaccurate medical information in the region of the teeth biting surfaces of the CAT scan record.

SUMMARY

The present invention provides a method and apparatus for matching digital three-dimensional dental models with digital three-dimensional cranio-facial CAT scan records. By doing so, the inaccurate portions of a cranio-facial CAT scan record can be improved.

The assignee of the present invention, IRIS Development Corporation of Minnesota, has developed a method and apparatus for generating an accurate digital three-dimensional model of a patient's teeth and soft tissue from an impression. Such electronic model is commercially available under the designation, and will be referred to herein as, E-MODEL.

The present invention utilizes a modified impression tray used in connection with the E-MODEL. The modified impression tray is held in a patient's mouth during the CAT scan. The tray is arranged and configured to include means for providing reference or registration points in the CAT scan. The tray includes a dental impression material which, subsequent to the CAT scan, is removed from the patient's mouth and placed on a table of an X-Y-Z scanning machine to permit accurate scanning of the negative impression on the impression tray by the scanner of the scanning machine. In this manner, a set of electronic data related to the patient's teeth and surrounding soft tissues can be generated (e.g., the E-MODEL). The means for providing registration points are also included in the set of electronic data for the patient's teeth.

The following co-pending, commonly assigned applications are incorporated herein by reference and made a part hereof: Ser. No. 08/789,918, titled DENTAL SCANNING APPARATUS AND METHOD filed on Jan. 28, 1997; Ser. No. 09/311,436 titled "Buccal Impression Registration Apparatus, and Method of Use", filed on May 14, 1999; Ser. No. 09/312,417 titled SCANNING APPARATUS FIXTURE FOR HOLDING IMPRESSION TRAYS, filed on May 14, 1999.

These and other advantages and features which characterize the present invention are pointed out with particularity in the claims annexed hereto and forming a further part hereto. However, for a better understanding of the invention, reference should be had to the following drawing and detailed description.

BRIEF DESCRIPTION OF THE DRAWINGS

Referring to the drawing, wherein like numerals represent like parts throughout the several views:

FIG. 18 is a side view of a registration fixture in accordance with the present invention.

FIG. 19 is a sectional view taken along line 19-19 of FIG. 18 illustrating the left hand locking fixture.

FIG. 23 is an illustration of a modified registration tray 300 of FIG. 3a.

FIG. 24 is an illustration of the resulting combined CAT scan and electronic E-MODEL data.

DETAILED DESCRIPTION

As note above the principles of the present invention provide for a method and apparatus for reducing the inaccuracies of cranio-facial CAT scan images. The present invention provides for a registration and matching technique between digital three-dimensional dental models with digital three-dimensional cranio-facial CAT scan records.

Although the cranio-facial example will be used herein, it will be appreciated that the principles of the present invention may be employed in connection with other parts of the human body. For example, the principles can be applied to other objects and/or areas wherein a deficiency is found in taking a CAT scan image, which deficiency can be improved by taking an impression of the object and/or area. A combined image can then be generated after registration of the two images.

A detailed discussion of the present invention will now be deferred pending a discussion of the method and apparatus utilized in connection with generating a digital image from an impression (e.g., an E-MODEL).

a. Generating the E-MODEL

Figure 1:
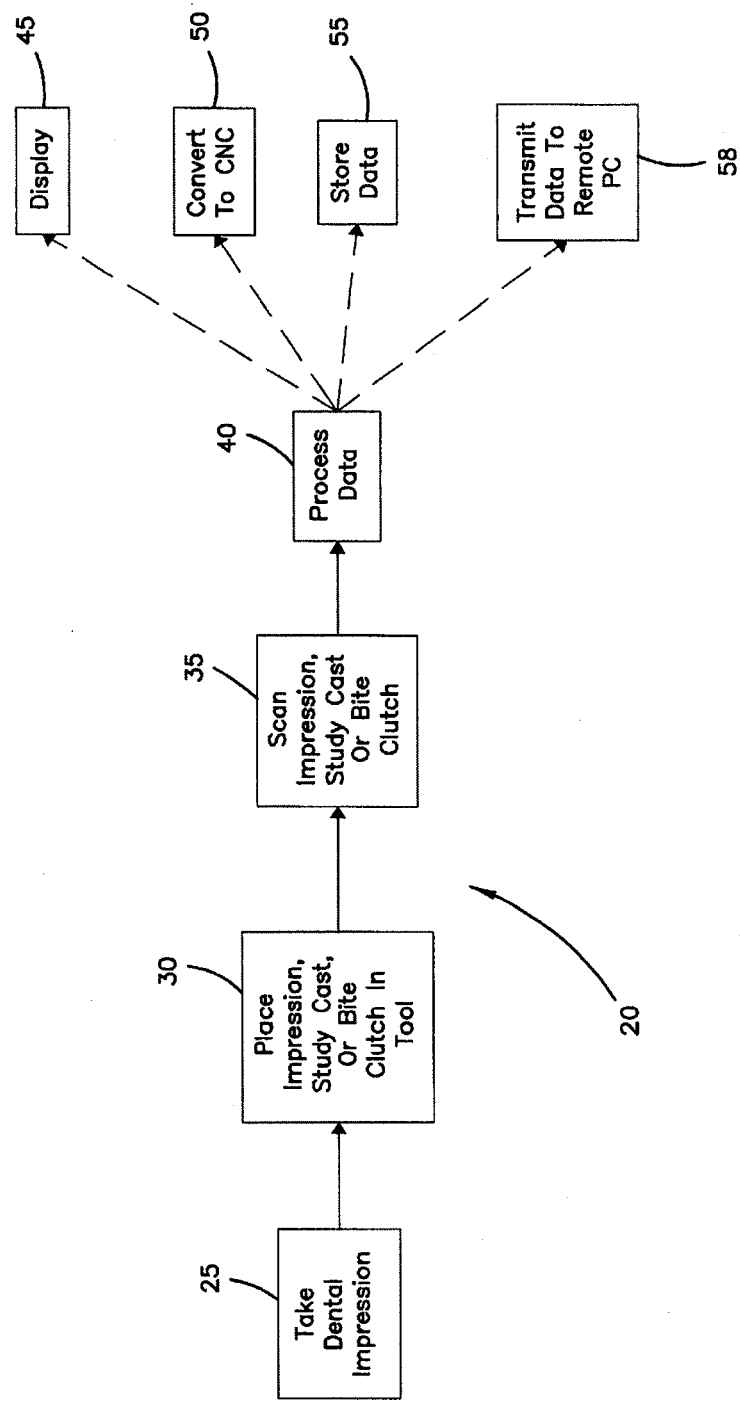
FIG. 1 illustrates the method steps 20 used to obtain the digital three-dimensional image of the patient's teeth and surrounding soft tissue.
Figure 2A:
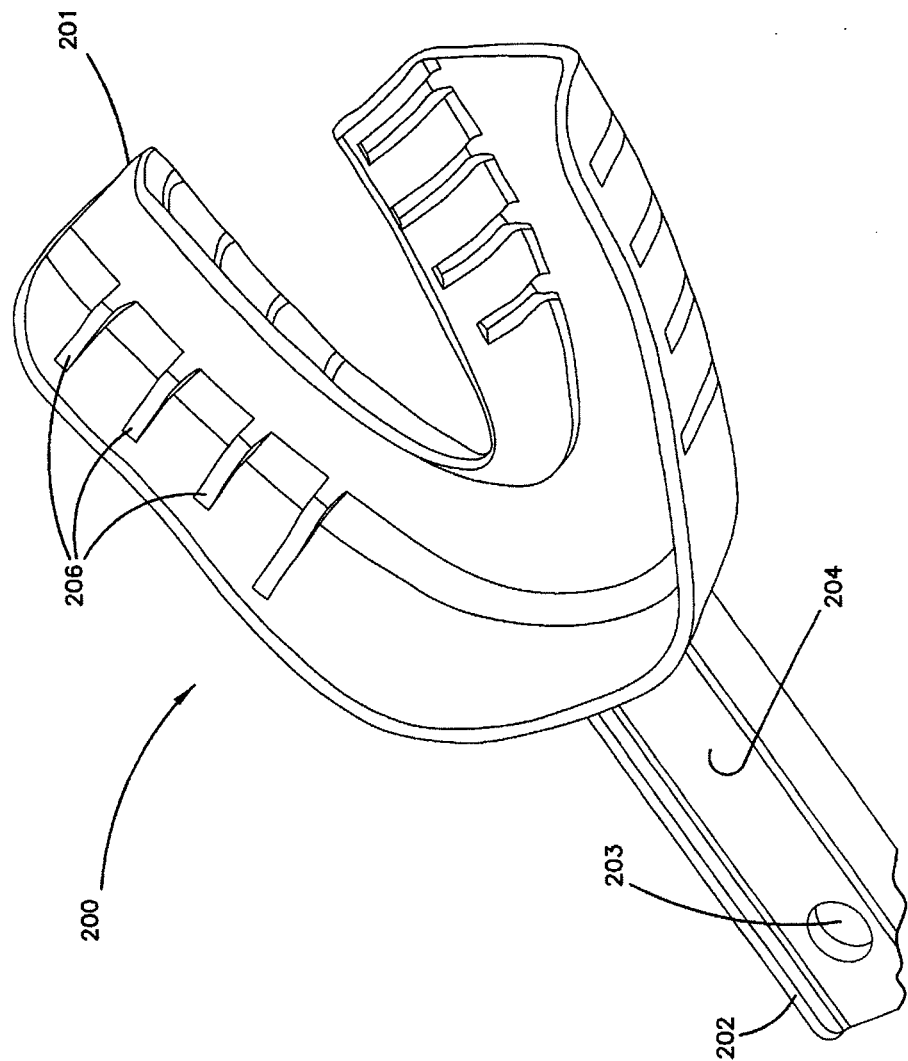
FIGS. 2a and 2b illustrate perspective views of lower 200 and upper 220 impression trays, respectively, used in connection with the present invention.
Figure 2B:
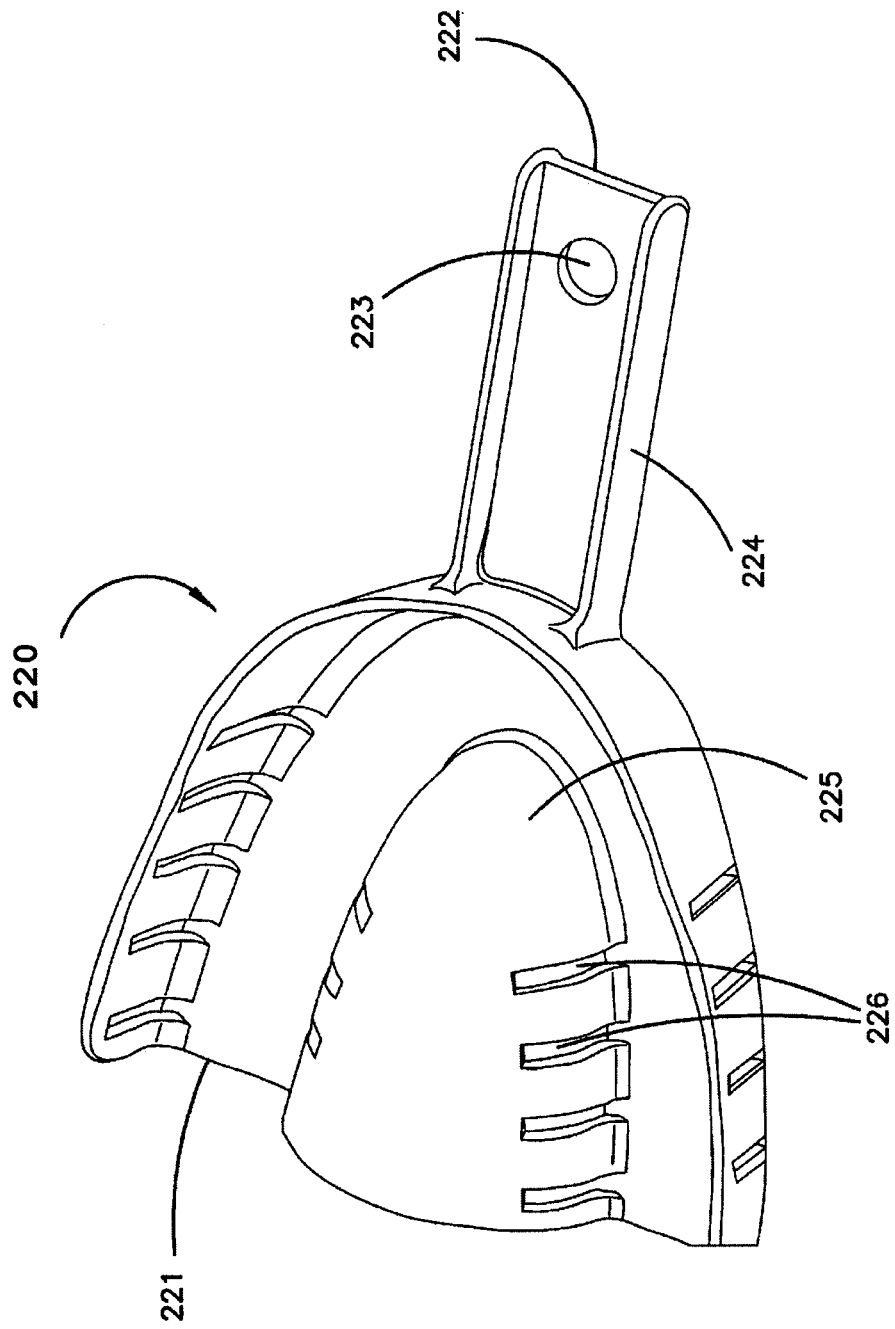
Figure 3A:
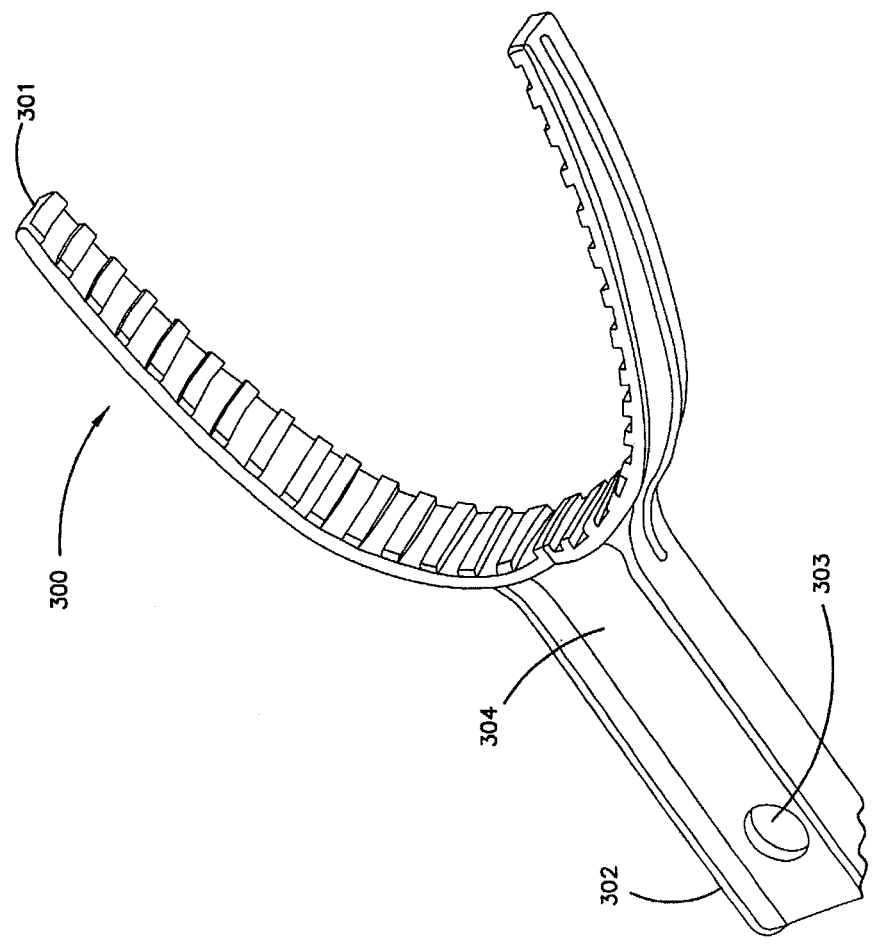
FIG. 3a illustrates a perspective view of a registration tray 300 used in connection with the present invention.
Figure 3B:
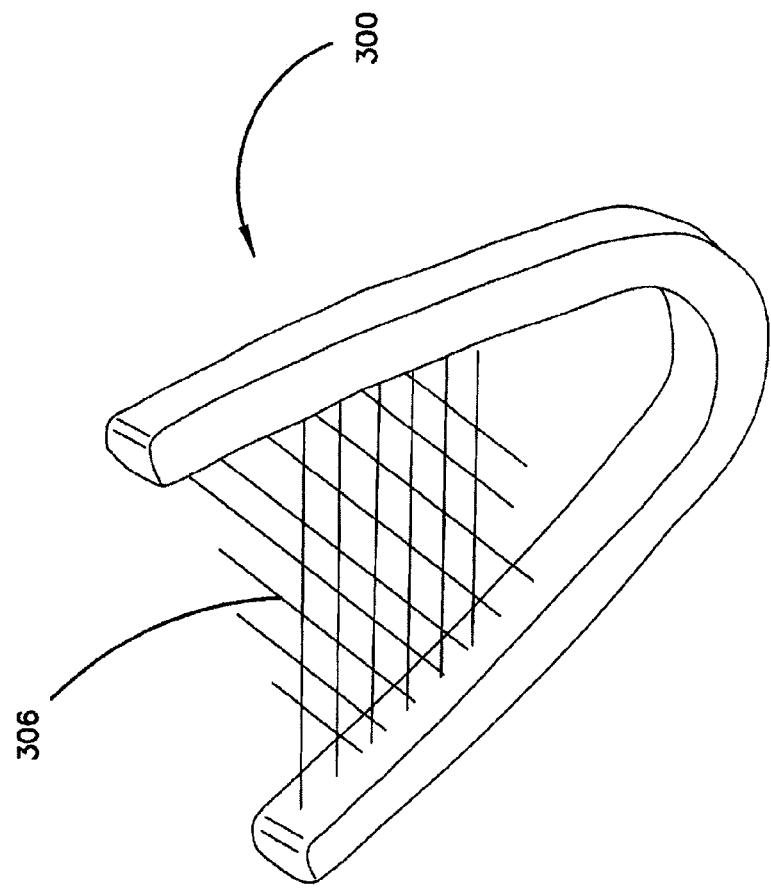
FIG. 3b diagrammatically illustrates the preferred arrangement and configuration of the impression material retaining mesh 306 used in connection with tray 300.

Referring first to FIG. 1, the overall method used with respect to generating the E-MODEL is illustrated generally by the designation 20. First, at block 25, a dental impression of a patient's teeth and surrounding soft tissues (hereafter referred to collectively as "teeth" for convenience) is taken. The impression material hardens, forming a negative image of the teeth. The lower 200 and upper 220 trays used in connection with taking the impression are described below and are best seen in FIGS. 2a and 2b respectively. The bite/clutch tray 300 used in connection with determining the correct spatial orientation and relationship between the upper and lower impressions is described below and is best seen in FIGS. 3a and 3b.

At block 30, the impression tray 200 or 220 is placed in the tool or fixture 600 (described below and best seen in FIGS. 5 and 7-17). The fixture 600 is used to securely hold the tray 200, 220, and/or 300 during the scanning step. The fixture 600 may also aid the scanning step by helping rotate the mold so that the image data can be properly generated. It will be appreciated that during this step at least one of the trays 200 and 220 include the hardened impression material which defines a negative image impression or mold of a patient's teeth.

Next at block 35, the scan of the impression occurs. In the preferred embodiment, a scanner manufactured by Laser Design Inc. of Minneapolis, Minn. designated as model number 8849648 may be used. The general operation employed by this type of scanner is generally described in U.S. Pat. No. 5,124,524 (which is hereby incorporated herein by reference). However, the preferred type of laser scanner is generally referred to as a line scanner device. It will be appreciated that for a complete study cast of the upper and lower teeth, two scans of the negative image impressions occur (i.e., one lower and one upper). Further, in order to properly reference the two sets of teeth together, a scan of the bite tray 300 impression also takes place.

Figure 6:
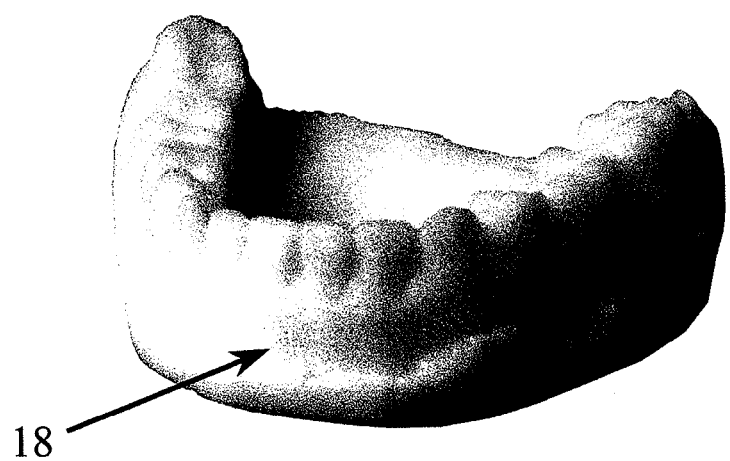
FIG. 6 is a perspective view of a positive image of a scanned portion of a study cast.

Referring now to FIGS. 1 and 6, at block 40 the image data is processed by processor 501. Such processing may include converting the negative image scan data into a positive image for display on a video display unit 503 (at optional block 45); converting the negative image scan data into CNC or other format of output for use by a fabrication device 507 (also known as a prototyping apparatus) (at optional block 50); storing the negative image scan data in a memory location or device 504 (at optional block 55); and/or transmitting the negative image scan data to a remote processor 505 via modem block 502 (at optional block 58).

In the preferred embodiment, one commercially available software package which may be used to generate three dimensional images from the line scan data is the package sold under the designation DataSculpt software available from Laser Design Inc. of Minneapolis, Minn.

Turning now to FIGS. 2a and 2b, the lower impression tray 200 and upper impression tray 220 are illustrated. The trays 200 and 220 are shown without impression material located thereon in order to more clearly illustrate the size and configuration of the respective trays. The trays 200 and 220 are generally horseshoe shaped with an elongate member 204 and 224 (respectively) integrally attached to and extending away from the arcuate portion of the horseshoe section. The elongate members 204 and 224 are generally within the same mean plane formed by the horseshoe section. However, those of skill in the art will appreciate that other locations and arrangements may be utilized. The upper tray 220 also includes a domed element 225 which is integrally formed and connects the interior portion of the horseshoe section of the tray 220.

Each of the trays 200 and 220 also includes a first end 201 and 221 (respectively) which is inserted into a patient's oral cavity during the process of taking the impression and a second end 202 and 222 (respectively) which includes a handle for helping insert and remove the trays. Located proximate the second ends 202 and 222 are holes 203 and 223 (respectively) which are arranged and configured to aid in the registration process of the scanning procedure (i.e., the holes 203 and 223 on the handles may be used in conjunction with the mounting fixture 600). However, including such holes 203 and 223 and/or using the holes in the registration process is optional.

Slots 206 and 226 are formed in the lower and upper trays 200 and 220 (respectively) to aid in the expansion of the impression material when a patient bites into the same, as well as helping retain the impression material on the tray 220 and 226 (and in a fixed manner) after removal from a patient's mouth and during scanning. Only several of the plurality of slots 206 and 226 are designated by the reference numerals in the Figures for the purpose of clarity. Also, those of skill in the art will appreciate that the number and arrangement of the slots 206 and 226 may be changed, with the slots 206 and 226 shown in FIGS. 2a and 2b being illustrative.

The trays 200 and 226 are preferably constructed by means of plastic injection molding process and of a material suitable for medical and dental purposes. Such material should also be selected to be rigid enough to hold the impression material in a stable fashion during scanning and be capable of being sanitized or sterilized.

Turning now to FIGS. 3a and 3b, the bite registration tray 300 is illustrated. Tray 300 is shown without impression material located thereon in order to more clearly illustrate the size and configuration of the tray. The tray 300 is generally horseshoe shaped with an elongate member 304 integrally attached to and extending away from the arcuate portion of the horseshoe section generally in the same mean plane formed by the horseshoe section.

Tray 300 includes a first end 301 which is inserted into a patient's oral cavity during the process of taking the impression and a second end 302 which includes a handle for helping insert and remove the tray 300. Located proximate the second end 302 is hole 303 which is arranged and configured to aid in the registration process of the scanning procedure (i.e., the hole in the handle may be used in conjunction with the mounting fixture 600). However, including such hole 303 and/or using the hole in the registration process is optional.

FIG. 3b illustrates the bite tray 300 without the elongate member 304 and including an impression retaining mesh material 306 generally located within the horseshoe section. The material 306 is used to retain the impression material on the tray. It will be appreciated that this configuration allows a patient to bite into the impression material on either side of the mean plane formed by the horseshoe portion of tray 300 to register the upper and lower impressions relative to one another so that study casts, visual displays, etc. can be created with the proper spatial relationships. In the preferred embodiment, tray 300 is constructed in a manner similar to that described above in connection with trays 200 and 220.

Figure 4:
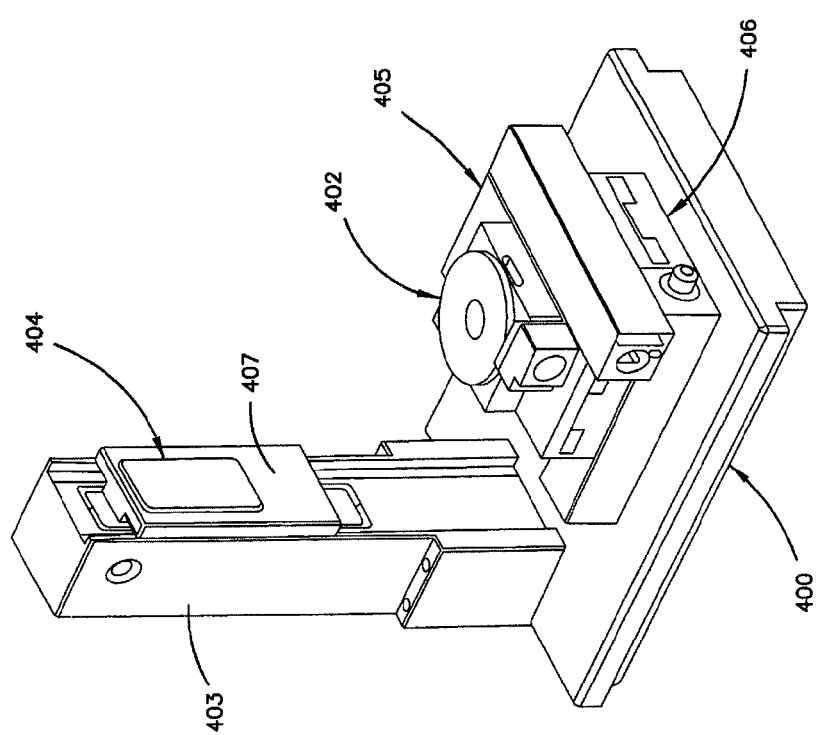
FIG. 4 illustrates a perspective view of a preferred embodiment base 400 and X-Y-Z axis devices 401 used in connection with scanner 60.
Figure 5:
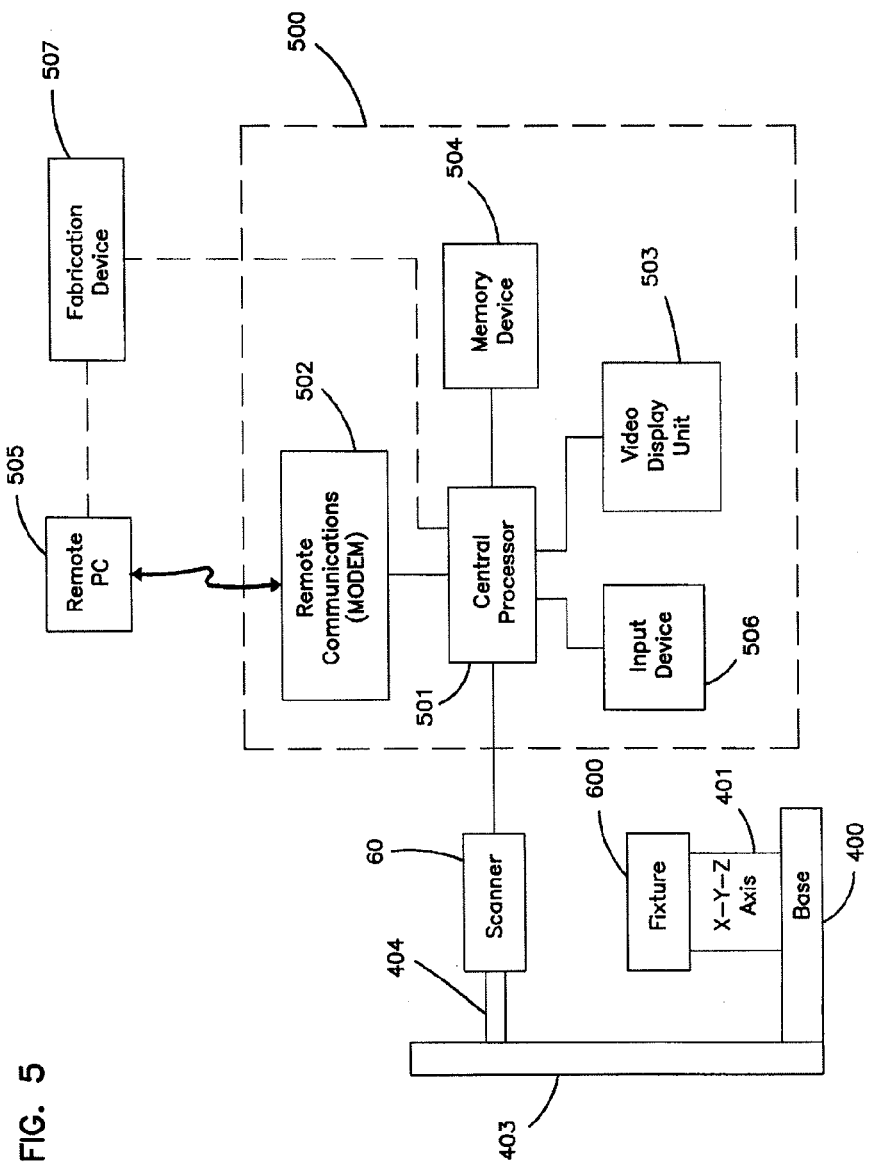
FIG. 5 diagrammatically illustrates the functional blocks associated with the processor, memory, and remote computer associated with processing the data from the scanner 60.

The tooling or fixture 600 is shown as a functional block in FIG. 5. In the preferred embodiment, the fixture 600 is arranged and configured to securely hold the trays 200, 220, and 300 while rotating and/or moving on the stage 402 (best seen in FIG. 4 and described further below) as the array of negative image electronic data from the negative impression (s) is being generated by the scanner 60.

With reference now to FIGS. 7-13, a first embodiment of the fixture or tooling 600 is illustrated. As shown, the fixture 600 is mounted on the stage 402 of the scanning machine, where the table is preferably capable of rotary as well as tilting movements in a manner generally known in scanning machines. The fixture 600 includes a base member 601 mounted on the stage, and a locking fixture 602 detachably connected to the base member 601.

Figure 7:
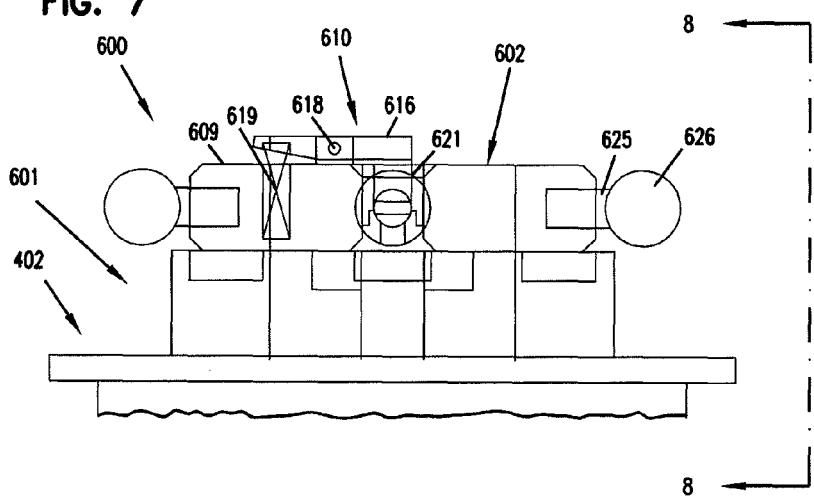
FIG. 7 is a side view of a fixture or tooling for holding an impression tray or study cast on the table of the scanner.
Figure 8:
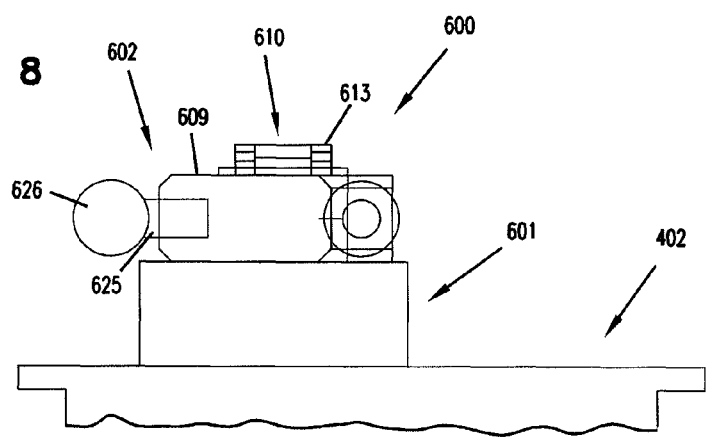
FIG. 8 is a side view looking in the direction of line 8-8 in FIG. 7.
Figure 11:
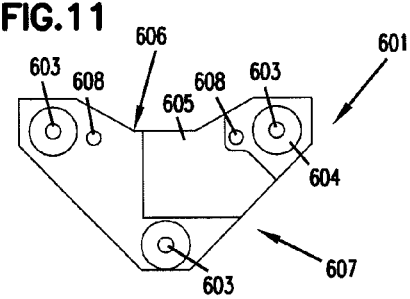
FIG. 11 is a top view of a base member for the tooling.
Figure 12:
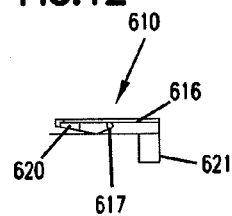
FIG. 12 is a side view of the pivoting lever used with the tooling of FIGS. 7-8.
Figure 13:
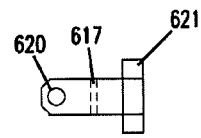
FIG. 13 is a top view of the pivoting lever.

As best seen in FIG. 11, the base member 601 is generally triangular in shape and made from a solid, metal material. Three throughholes 603 are formed in the base member and are aligned with corresponding threaded holes (not shown) in the stage 402. Fasteners (not shown), such as cap screws or the like, are then disposed in the throughholes 603 and threaded into the threaded holes in the stage 402 in order to fasten the base member 601 to the stage. The throughholes are preferably countersunk 604, so that the fasteners do not extend above the top surface of the base member 601, thus permitting the locking fixture 602 to contact the top surface of the base member 601 as shown in FIG. 7. A cut-out section 605 is formed in the base member 601 extending generally from a front 606 of the base member to a rear 607 of the base member. Further, a pair of locating holes 608 are formed in the base member 601 between the cut-out section 605 and a pair of the throughholes 603. The purposes of the cut-out section 605 and the locating holes 608 will become apparent later in the description.

The locking fixture 602 has the same overall shape as the base member and in the preferred embodiment is made from the same metal material. It will be appreciated that other materials might be selected which provide the necessary rigidity and strength to properly secure the trays during scanning. The locking fixture 602 includes a body portion 609 and a clamp means 610 disposed on the body portion for clamping one of the trays 200, 220, and 300 on the body portion to securely hold the tray during the scanning process.

Figure 9:
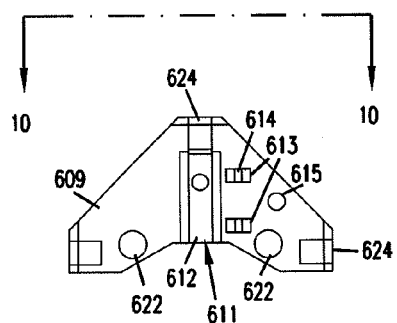
FIG. 9 is a top view of a locking fixture for the tooling in FIGS. 7 and 8.
Figure 10:
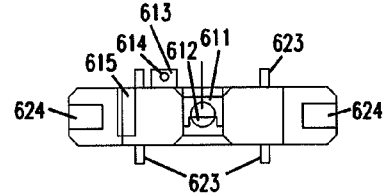
FIG. 10 is a side view looking in the direction of line 10-10 in FIG. 9.

With reference now to FIGS. 9 and 10, the details of the body portion 609 are illustrated. The body portion 609 includes a lowered channel area with side walls defining a groove 611. The groove 611 extends from a front of the body portion toward the rear thereof, but in the preferred embodiment stops short of the rear. The groove 611 is sized so as to receive the elongate handle members 204, 224, and 304 of the trays therein. A generally planar surface 612 defines the bottom of the groove 611, and forms a surface against which the elongate handle members are clamped.

A pair of spaced flanges 613 extend upwardly from the top surface of the body portion on one side of the groove. Each flange 613 includes a pivot hole 614 formed therein extending generally parallel to the groove 611. Further, a hole 615 is formed in the body portion through the top surface thereof. The preferred location of the hole 615 is on an imaginary line running perpendicular to the groove 611 and generally midway between the flanges 613. The hole 615 lies on the distal end of the imaginary line relative to the flanges 613. The clamp means 610 includes a lever 616 with a hole 617 located proximate the midpoint thereof. The lever 616 is pivotally connected between the flanges 613 by a pivot shaft 618 extending through the holes 614 and 617. A coil spring 619 is disposed within the hole 615, and an end of the spring is disposed within a recess 620 provided in the end of the lever to bias the lever in a clamping direction. The opposite end of the lever includes a clamp block 621 connected thereto which extends into the groove 611 and is generally parallel therewith to engage with the handle members of the trays.

As will now be apparent to those of ordinary skill in the art, a tray is clamped by the locking fixture 602 by the following steps. First, a downward force is applied on the end of the lever against the bias of the spring so as to raise the clamp block. Second, the handle member of the tray is then fully inserted into the groove between the clamp block and the planar surface 612. Third, the lever is then released, with the spring biasing the clamp block into engagement with the handle member, thus clamping the handle member between the clamp block and the planar surface. The tray is thus securely fixed for subsequent scanning by the scanner 60.

It is to be realized that the groove 611, surface 612 and surrounding structure could have other shapes and configurations so as to accommodate any type of impression tray handle. For instance, if the impression tray handle were completely flat, the surface 612 could be modified so that the bottom of the groove 611 is completely flat to match the flat impression tray handle.

The biasing force of the spring should be sufficient to maintain a clamping force that is able to hold the weight of the tray and the impression material thereon. The fixture could also be used to hold a study cast for scanning by the scanner. The study cast would be provided with a handle member similar to the handle members 204,224 to permit the study cast to be clamped on the fixture 600.

As described above with reference to FIGS. 2a and 2b, separate trays 200,220 are used to generate an impression of the upper and lower sets of teeth. However, a two-sided impression tray could be used to simultaneously generate an impression of the upper and lower teeth. The two-sided impression tray would have a handle similar to the handles 204, 224. The two-sided impression tray may be secured to the fixture in the same manner as described above. However, once the tray is secured to the fixture and scanning commences, it is not desirable to move the tray relative to the fixture (e.g., since this may affect the results of the scanning). Therefore, since the scanner scans only one side of the two-sided impression tray at a time, the other side of the tray must be able to be positioned for scanning by the scanner, without removing the tray from the fixture.

The fixture 600 of the present invention is designed so as to accommodate such a two-sided impression tray. As shown in FIGS. 9 and 10, the body portion 609 includes a pair of holes 622 therein disposed on each side of the groove adjacent the front of the body portion, at corresponding locations to the locating holes 608 in the base member. A pair of locating pins 623 are suitably mounted in the holes 622 and extend past the top and bottom surfaces of the body portion. The pins 623 thus detachably connect the locking fixture 602 to the base member 601. In use, the two-sided tray is secured to the fixture in the manner previously described, with the fixture oriented as shown in FIG. 7. The upper impression formed on the tray is then scanned. In order to scan the lower impression, the locking fixture 602 is lifted upward until the pins that extend from the bottom of the fixture are disengaged from the locating holes 608. The locking fixture 602 is then "flipped over" and re-secured to the base member by inserting the pins that extend from the top of the fixture 602 into the locating holes. The cut-out section 605 in the base member accommodates the flanges 613 and lever 616 when the locking fixture is flipped over to permit the top surface of the body portion to contact the top surface of the base member. Scanning of the lower impression can then commence. Thus it can be seen that the location and orientation of the two-sided tray on the fixture 600 is not altered, thus improving the results of the scanning of both impressions.

The body portion 609 also includes a plurality of holes 624 therein that receive pins 625 connected to tooling balls 626. The tooling balls are used for reference purposes by the scanner during initializing of the scanning sequence.

An alternate fixture 600' is illustrated in FIGS. 14-17. The alternative fixture 600' is useful for holding impression trays and study casts that do not include a handle member. The fixture 600' includes a base member 601' of generally the same overall structure as the base member of the first embodiment, as illustrated by dashed lines in FIG. 15, with the base member 601' being secured to the stage 402 in the same manner as the first embodiment. A locking fixture 602' is secured to the base member 601' for clamping the tray or study cast thereon. The base member 601' is preferably identical to the base member 601 to permit interchangeable use of the locking fixtures 602, 602'.

The locking fixture 602' includes a body portion 640 and a clamp means 641 disposed on the body portion for clamping a handleless tray or study cast on the body portion to securely hold the tray or study cast during the scanning process.

Figure 15:
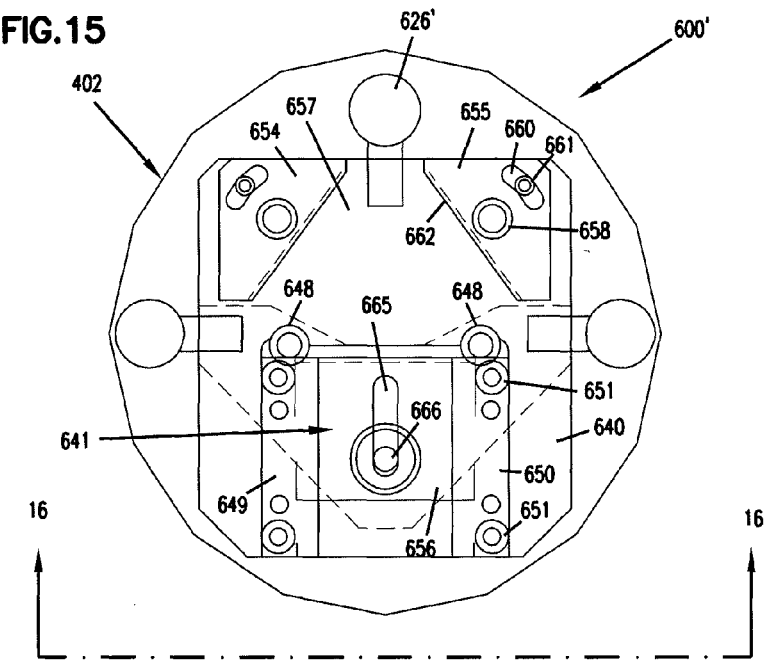
FIG. 15 is a top view of the second fixture or tooling looking in the direction of line 15-15 in FIG. 14.
Figure 17:
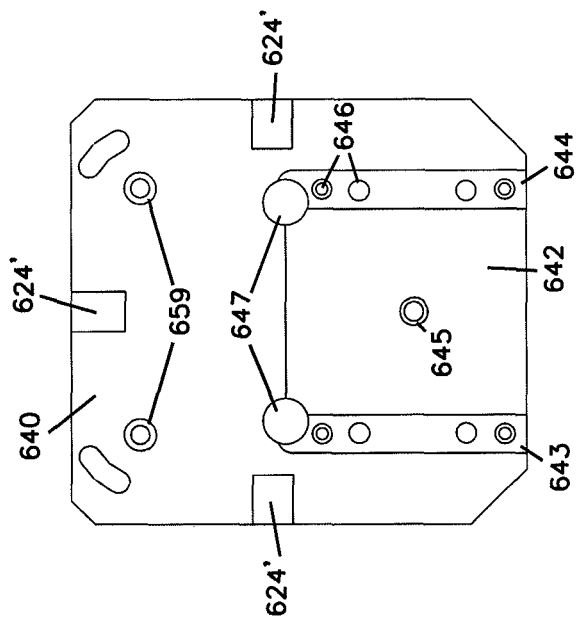
FIG. 17 is a top view of a body portion of the fixture or tooling.
Figure 16:
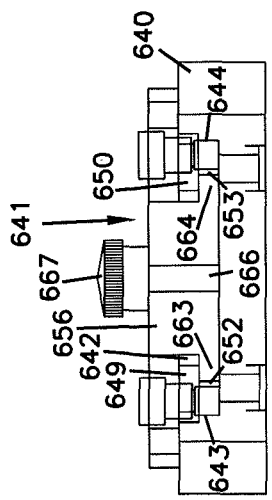
FIG. 16 is a side view looking generally in the direction of line 16-16 in FIG. 15.

With reference to FIGS. 15-17, it can be seen that the body portion 640 is generally rectangular in shape and includes a recessed central portion 64Z with a pair of raised shoulders 643, 644 extending along each side of the recessed portion.

An internally threaded hole 645 is formed in the center of the recessed portion 642, and a series of threaded holes 646 are formed in each raised shoulder 643, 644. Further, a pair of holes 647 are formed through the body portion 640 at the ends of the shoulders 643,644 at locations corresponding to the locating holes 608 in the base member 601', to permit attachment of the body portion to the base member using fasteners 648, such as cap screws or the like, by inserting the fasteners through the holes 647 and into threaded engagement with the locating holes 608.

A pair of rectangular bars 649, 650 are fastened to the top surfaces of the shoulders 643, 644 by suitable fasteners 651 extending through the bars and into engagement with the holes 646. The bars 649, 650 have a length generally equal to the length of the shoulders, but are wider than the shoulders so as to overhang the top surface of the recessed portion 642 to thus define a pair of tracks 652, 653 between the overhanging portion of the bars and the surface of the recessed portion.

The clamp means 641 comprises a pair of clamp blocks 654, 655 fixed to the body portion, and a slide block 656 slidably mounted in the recessed portion 642, with a clamp section 657 formed between the blocks 654-656.

Figure 14:
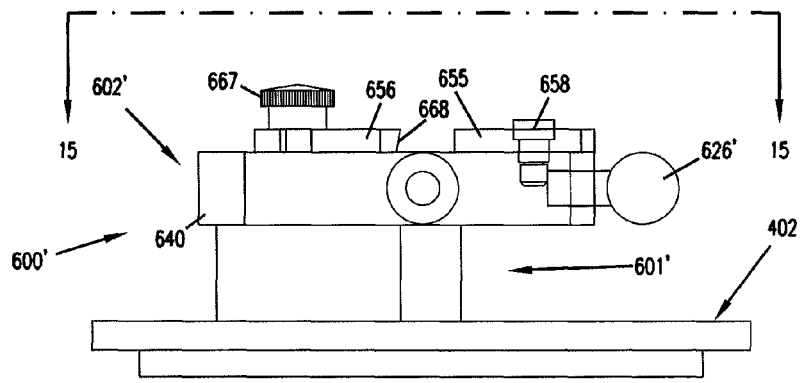
FIG. 14 is a side view of a second embodiment of the fixture or tooling.

As best seen in FIGS. 14 and 15, each clamp block 654, 655 is fastened to the top of the body portion 640 by a fastener 658 which engages with a threaded hole 659 in the body portion. Each clamp block further includes an arcuate slot 660 formed therethrough which receives a pin 661 that is rigidly connected to the body portion in any suitable manner. The angular position of the clamp blocks can be adjusted by loosening the fasteners 658 and pivoting the clamp blocks within the extent permitted by the arcuate slots 660, and then re-tightening the fasteners 658. Further, each clamp block includes a clamping surface 662 that faces toward the clamp section. The clamping surfaces 662 are angled slightly downward relative to a vertical axis (as illustrated by dashed lines in FIG. 15) such that when a tray or cast is clamped in the clamping section 657, a downward force is generated on the tray or cast.

The slide block 656 is a generally rectangular member having a pair of side rails 663, 664 at the bottom thereof that are disposed for sliding movement within the tracks 652, 653. An elongated slot 665 is formed through the slide block generally parallel to the side rails, and a threaded stud 666 is secured within the threaded hole 645 of the recessed portion 642 and extends through the slot 665 beyond the top surface of the slide block. A locking knob 667 is threaded onto the end of the stud for fixing the location of the slide block.

It should be apparent that by loosening the knob 667, the slide block can be slid back and forth within the extent permitted by the slot 665, with the side rails being guided within the tracks. When a dental member, such as a tray or cast, is to be fixed within the clamping section, the member is placed on the clamping section, and the slide block slid forward until it engages the member. The position of the slide block is then fixed by tightening the knob 667. Like the clamping surfaces 662 of the clamp blocks, the slide block includes a clamping surface 668 that faces the clamping section, with the clamping surface being angled downward relative to the vertical direction (as seen in FIG. 14) to provide a downward force on the dental member when clamping occurs.

The body portion 640 is further provided with holes 624' to permit mounting of tooling balls 626', in the same manner as in the first embodiment.

Next, reference should be had to FIGS. 4 and 5 where a more detailed discussion of a scanner, its components and operation will be presented. In FIGS. 4 and 5, the scanner is designated generally at 60. As noted above, the scanner 60 and its operation is described in detail in U.S. Pat. No. 5,124, 524. Also shown in FIG. 4 is the Z-axis column 407 which preferably provides precise vertical linear motion with a screw and nut assembly. Scanner mounting member 404 is operatively connected to the Z-axis column 407. Rotary stage 402 preferably provides precise rotational movement in the range of 0.001" quadrature resolution. The stage 402 can also have tilt movements, in addition to its rotary movements. X-axis stage 406 and Y-axis stage 405 provide X and Y coordinate control and preferably use lead screw assemblies. Column 403 is attached to base 400 and supports the scanner 60. In FIG. 5, the X axis stage 406, Y axis stage 405, the Z axis stage 407 and the rotational stage 402 are together referred to as block 401.

Still referring to FIG. 5, the functional blocks of the electronic components of the present invention are illustrated. The components include a computer 500 which preferably includes a processor 501, a video display unit 503, a memory device 504, a user input device 506 (e.g., a mouse and/or keypad), and a modem 502. Also illustrated is a remote computer 505, a fabrication device 507, and the scanner 60 (and its attendant X-Y-Z axis controllers and motors).

It will be appreciated by those of skill in the art that the computer 500 may be a personal computer (e.g., a Pentium based PC) or a special purpose computer. Further, the video display unit 503 may include any number of display devices such as cathode ray tubes, LCD displays, etc. Still further, the memory device 504 may include hard drives, floppy drives, magnetic tape, CD-ROM, random access memory, and read-only memory devices. Further, the modem 502 is illustrated to show a communications capability. Such capability may also be by way of a network, etc.

Fabrication device 507 may be connected directly to the computer 500 or may be connected to a remote computer 505. The fabrication device 507 may be any number of devices which can utilize computer generated data and create a three-dimensional object from such data. One example of such a machine are the devices utilizing stereo lithography technology manufactured by 3-D Systems of Valencia, Calif. under the model designations SLA-250 and SLA-500. Another example is the device utilizing filament technology (fused deposition modeling) manufactured by Statasys Corporation of Minneapolis, Minn. under the model designation FDM-1500.

In operation the array of negative image scan data is generated by the scanner 60 and provided to the processor 501. The negative image scan data may be saved in a memory device 504 as a permanent record of the baseline condition of the patient's teeth, or temporarily prior to one of several other options. For example, the data may be converted to a positive image and stored in that fashion as a permanent record of the baseline condition. Alternatively, the positive image may be displayed on the video display unit 503 for teaching or educational purposes with the patient. Still further, the positive information data may be transmitted to a remote PC 505 for storage, study by a consulting dentist (or physician), or fabrication of a study cast by fabrication device 507. The fabrication device 507 may optionally be connected directly to computer 500. These and other options may be selected by the computer 500 user via the input device 506.

It will be further appreciated that the resulting positive image data can be converted into a language acceptable to a three-dimensional software program (i.e., the .stl format). For example, 3d Studio by AutoDesk might be employed to view the image on either computer 500 or remote PC 505.

The programming operation of the processor 501 provides for scanning each of the upper and lower impressions and the bite registration impression. These scans provide the information necessary to create an electronic equivalent of the prior art physical study casts. By using negative image impressions and a line scanner, high resolution and speed are gained wherein high quality study casts may be generated by a fabrication device 507 thereby replacing older methods of constructing the same. Although such fabricated casts may still be saved, since the data is generated and stored electronically, the problems associated with storage of prior art study casts may be reduced and/or eliminated. Further, the data may be used any number of times in different ways to accomplish a more robust practice.

It is contemplated that other impressions of a patient's body may be taken to form a negative image mold and subsequently mounted on the fixture for scanning by the scanner.

FIGS. 18-21 illustrate a registration fixture 700 that is used to simultaneously hold study casts of upper and lower sets of teeth while enabling the study casts to be brought into precise registration with each other to reflect the bite registration of the patient. The fixture 700 includes a rigid, L-shaped support base 702 made from a metal material, and includes a horizontal plate portion 704 and a vertical plate portion 706 extending vertically from the plate portion 704.

The support base 702 is adapted to be mounted on the base member 601 illustrated in FIGS. 8-13 upon removal of the locking fixture 602. To accomplish such a mounting, the support base 702 includes a pair of threaded cap screws 708 extending through the horizontal plate portion 704 and adapted to extend through a pair of the throughholes 603 formed in the base member 601 and into threaded engagement with the corresponding threaded holes formed in the stage 402. In this manner, the support base 702 is secured to the base member 601, with both the base member 601 and support base 702 being secured to the stage 402. A pair of cylindrical stand-offs 710 are connected to the bottom of the plate portion 704 to space the fixture 700 from the stage 402 as well as to help stabilize the fixture 700.

A left, or first, locking fixture 712 is secured to the vertical plate portion 706 and extends generally parallel thereto. The construction of the locking fixture 712 is generally identical to the locking fixture 602' in FIGS. 14-17, and thus includes a body portion associated therewith, as well as clamp mechanism, similar to the body portion 640 and clamp means 641 of the locking fixture 602'. Since the details of the locking fixture are completely described in relation to FIGS. 14-17, the details of the locking fixture 712 are not shown in FIGS. 18-21. The locking fixture 712 is intended to securely hold one of the study casts of the upper and lower sets of teeth, preferably the study cast for the lower set of teeth, on the fixture 700. However, it is to be realized that the locking fixture 712 could hold the study cast of the upper set of teeth if desired.

With reference to FIGS. 18 and 19, it is seen that the locking fixture 712 is secured to the plate portion 706 via a cap screw 714 (illustrated in dashed lines in FIG. 18) that extends through a countersunk hole 716 provided in the locking fixture 712 and through a hole 718 provided in the plate portion 706. The cap screw 714 is threaded at one end and an adjustment knob 720 threads onto the threaded end of the cap screw. The intermediate portion of the cap screw 714 is unthreaded and forms a bearing about which the locking fixture 712 is able to pivot when the knob 720 is loosened, whereby the locking fixture 712 is pivotable back and forth about the axis A defined by the cap screw 714 and extending perpendicular to the plane of FIG. 19 as shown by the arrow 721 therein. Thus, by loosening the knob 720, the angular orientation of the locking fixture 712, and the study cast held thereby, can be adjusted as desired. Once the desired angular orientation is achieved, the locking fixture 712 is then fixed in that orientation by tightening the knob 720 which clamps the locking fixture 712 to the plate portion 706 and prevents further movement of the fixture 712.

A pair of elongate, cylindrical guide rods 722a, 722b are fixed to the locking fixture 712 adjacent the bottom thereof, such that the guide rods 722a, 722b pivot with the fixture 712. The guide rods 722a, 722b are substantially parallel to each other, with one end of each rod 722a, 722b being fixed to the fixture 712, and a second, distal end 724 of each guide rod being spaced from the fixture 712. The guide rods 722a, 722b each have substantially smooth, low friction outer surfaces for a purpose which will become apparent later in the description.

A right, or second, locking fixture 726 is provided on the registration fixture 700. Like the first locking fixture 712, the construction of the locking fixture 726 is generally identical to the locking fixture 602' in FIGS. 14-17, and thus includes a body portion associated therewith, as well as clamp mechanism, similar to the body portion 640 and clamp means 641 of the locking fixture 602'. Since the details of the locking fixture are completely described in relation to FIGS. 14-17, the details of the locking fixture 726 are not shown in FIGS. 18-21. The locking fixture 726 is intended to securely hold one of the study casts of the upper and lower sets of teeth, preferably the study cast for the upper set of teeth, on the fixture 700. Of course, it is to be realized that the locking fixture 726 could hold the study cast for the lower set of teeth.

The second locking fixture 726 is mounted on the fixture 700 so as to be moveable toward and away from the first locking fixture 712, as shown by the arrow 728 in FIG. 18, so that the study cast held by the locking fixture 726 can be brought toward the study cast held by the locking fixture 712, so that the bite registration of the patient can be viewed. The second locking fixture 726 is also mounted on the fixture 700 so that it is adjustable relative to the first locking fixture 712, thereby enabling precise registration between the study casts.

Figure 20:
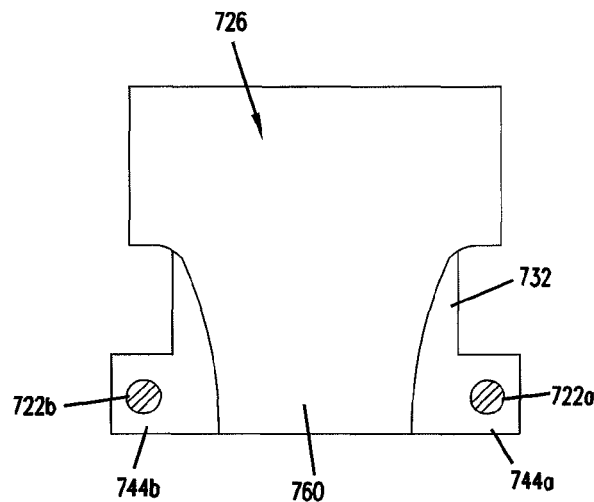
FIG. 20 is a sectional view taken along line 20-20 of FIG. 18 illustrating the right hand locking fixture.
Figure 21:
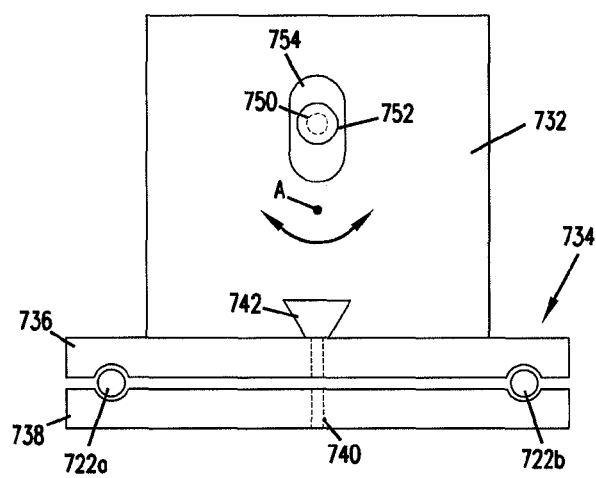
FIG. 21 is an end view taken along line 21-21 of FIG. 18 illustrating details of the guide rod clamp.

With reference to FIGS. 18 and 20-21, the details for mounting the locking fixture 726 for movements in the direction of the arrow 728 are shown in detail. A guide rod clamp 730 having a vertically oriented plate 732 is provided adjacent the locking fixture 726, with the plate 732 oriented generally parallel to the fixture 726. A clamp mechanism 734 is disposed at the base of the plate 732 for sliding engagement with the guide rods 722a, 722b. The clamp mechanism 734 includes an upper clamp portion 736 and a lower clamp portion 738 which together define a pair of channels for receiving the guide rods 722a, 722b. A threaded screw 740 extends upwardly from the lower clamp portion 738 and through the upper clamp portion 736, and an adjustment knob 742 is threaded onto the end of the screw 740.

It should be evident that by rotating the knob 742 in one direction, the clamping portions 736,738 are drawn together, thereby clamping the guide rods 722a, 722b between the clamp mechanism 734 and preventing sliding movement of the guide rod clamp 730 along the guide rods 722a, 722b. By rotating the knob 742 in the opposite direction, the clamping portions 736, 738 are loosened, thereby permitting the guide rod clamp 730 to freely slide along the guide rods 722a, 722b either towards or away from the first locking fixture 712 to a desired position where the guide rod clamp is subsequently fixed in position by rotating the knob in the tightening direction.

As evident from FIG. 18, the clamp mechanism 734 projects horizontally from the plate 732 to provide sufficient space for the knob 742 and actuation thereof. A pair of ears 744a, 744b are formed at the bottom edge of the plate 732, with the ears 744a, 744b thus being horizontally spaced from the upper and lower clamp portions 736, 738, whereby the guide rods 722a, 722b extend through the ears 744a, 744b as well as through the clamp portions 736, 738.

A block 746 is securely fixed to the face of the plate 732 that faces the first locking fixture 712. The block 746 is formed with a socket (not visible in the figures) that receives therein a substantially hemispherical ball 748 fixed on the back side of the second locking fixture 726. The ball 748 and corresponding socket in the block 746 thus form a ball joint by which the second locking fixture 726 is able to be adjusted relative to the guide rod clamp 730, and thus relative to the first locking fixture 712. Projecting from the end of the ball 748 is a threaded member 750 which extends through the plate 732, and a knob 752 is screwed onto the end of the member 750 for selectively fixing the position of the locking fixture 726.

As illustrated in FIG. 21, the plate 732 is provided with a slot 754 that is elongated vertically, as well as having a horizontal dimension that is greater than the diameter of the threaded member 750. The relatively large size of the slot 754 accommodates movement of the threaded member 750 as the second locking fixture 726 is pivoted. To enable clamping and fixing of the second locking fixture 726, as well as to provide a slight resistance to movement of the fixture 726 when the knob 752 is loosened, a coil spring 756 is disposed around the threaded member 750 between two washers 758.

It should be apparent that by rotating the knob 752 in one direction, the locking fixture 726 is clamped to the plate 732 and thereby fixed in position relative to the plate 732. By rotating the knob in the opposite direction, such as when adjustment of the orientation of the locking fixture 726 is desired, the locking fixture 726 is able to be adjusted to the desired orientation due to the movements permitted by the ball 748 and socket joint, with the coil spring 756 provided a certain resistance to the movement of the locking fixture 726. Once the locking fixture 726 has been suitably oriented, the knob 752 is once again tightened to fix the orientation of the fixture 726 and the study cast held thereby.

It is to be noted from FIG. 20 that the bottom edge 760 of the locking fixture 726 is suitably shaped such that the bottom edge 760 is disposed between the two guide rods 722a, 722b, so that the locking fixture 726 can pivot without interference from the guide rods 722a, 722b. It should be further apparent from FIGS. 18-21 that the second locking fixture 726 and the guide rod clamp 730 pivot simultaneously with the pivoting movements of the first locking fixture 712 about the axis A, since the guide rod clamp 730 is disposed on the guide rods 722a, 722b, and the second locking fixture 726 is connected to the guide rod clamp 730. In this manner, each of the study casts that are held by the locking fixtures 712, 726 can be simultaneously adjusted relative to the support base 702. Further, as described above, the orientation of the second locking fixture 726 can be adjusted independently of the first locking fixture 712, to enable precise registration between the study casts to be achieved.

In use of the registration fixture 700, the study cast of the lower set of teeth is mounted onto the first locking fixture 712, and the study cast of the upper set of teeth is mounted onto the second locking fixture 726. The clamp mechanism 734 is then loosened by loosening the knob 742, and the assembly formed by the guide rod clamp 730 and locking fixture 726 is slid along the guide rods 722a, 722b to bring the study cast of the upper set of teeth close to the study cast of the lower set of teeth held by the locking fixture 712. In the event of slight misalignment between the two study casts, the knob 752 is loosened, thereby allowing the locking fixture 726 to be pivoted so as to bring the study casts into precise registration. Once the correct registration is achieved, the knobs 742, 752 are tightened, thereby fixing the position of the locking fixture 726. To permit observation and analysis of the registered study casts from different orientations, the knob 720 is loosened, thereby enabling the assembly formed by the locking fixture 712, guide rods 722a, 722b, guide rod clamp 730 and locking fixture 726 to pivot about the axis A of the cap screw. Thereafter, the knob 720 is tightened to fix the orientation of the study casts.

b. Impression Tray with Registration Means

A preferred embodiment constructed in accordance with the principles of the present invention utilizes a dental impression tray that acquires the three-dimensional surface information of both upper and lower jaw occlusal surfaces in their closed bite position, or matched occlusal registration. The tray is arranged and configured to include the registration means. In the preferred embodiment, such means include three or more titanium markers glued to the dental impression tray so that the same dental impression tray can be repositioned in the patient's mouth prior to acquiring a MRI or CAT/CT scan record of the patient's oral anatomy.

Figure 23:
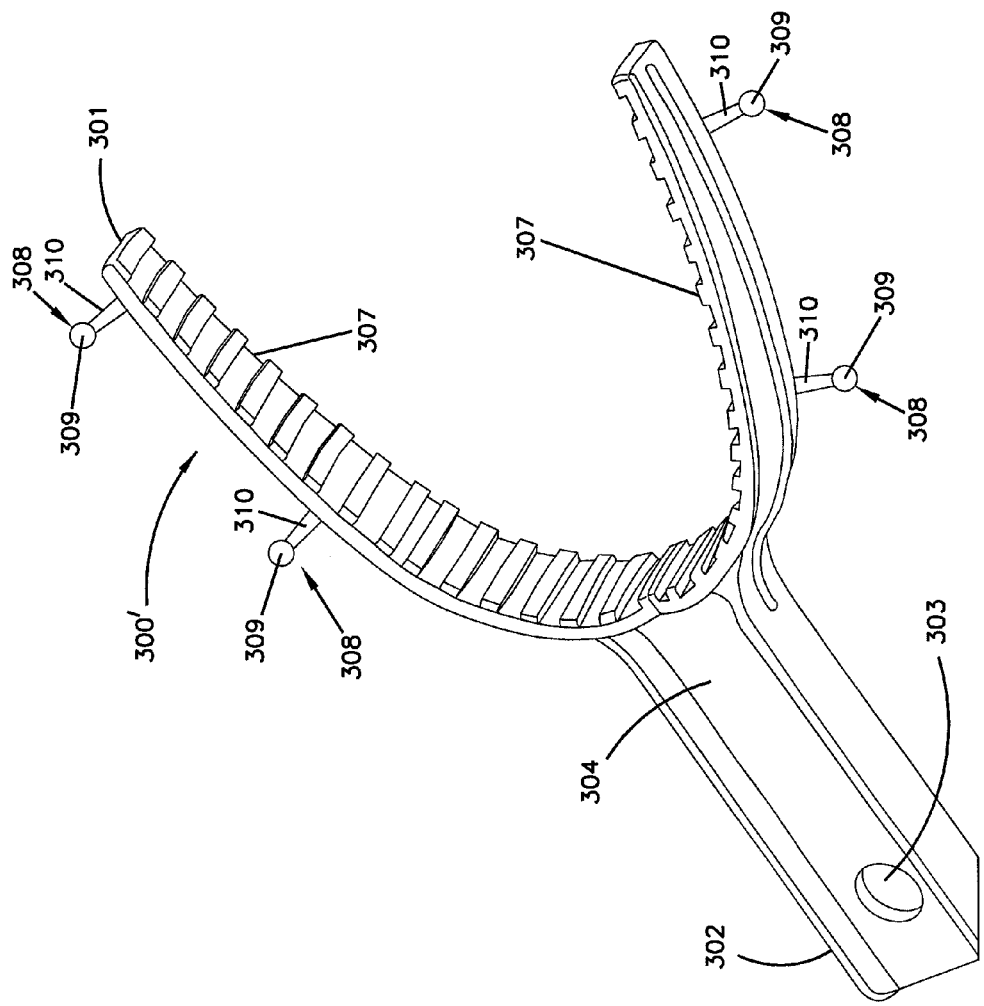

This modified improvement to the clutch dental impression tray is generally illustrated in FIG. 23 as 300'. The impression tray 300 without the registration means is illustrated in FIGS. 3a & 3b (and is described more detail in connection with those Figures above). FIG. 23 illustrates three or more titanium markers 308 that are located around the perimeter of the clutch tray arms 307 that contacts the patient's cheek surfaces. All of the titanium fiduciary markers 308 are preferably coplanar at the center line of the clutch dental impression tray that is parallel to the occlusal plane of the patient's teeth. The titanium fiduciary markers 308 may be permanently fixed to the clutch dental impression tray or they may temporarily fixed to the clutch dental impression tray by screw threads or other temporary fastening means to allow the titanium markers 308 to be recycled.

In the preferred embodiment, the titanium fiduciary markers 308 may be small spheres 309 (e.g., 4-8 mm in diameter) mounted on 1-2 mm diameter cylindrical pins 310 and connected to the clutch dental impression tray 300', or the titanium fiduciary markers 308 may be pointed cylinders. The geometry of the titanium fiduciary markers 308 may be of any shape that provides three or more repeatable points that can be dimensionally referenced in both electronic media; these media are the three-dimensional surface information of both upper and lower jaw occlusal surfaces in their closed bite position presented to the user on a computer monitor as shaded polygonal meshes and the MRI or CAT/CT scan record of the patient's oral anatomy presented to the user on a computer monitor as three-dimensional anatomical surfaces.

By using the titanium fiduciary markers 308 as common reference points the spatial matching of two medical records is accurately accomplished in one computer software package (e.g., 3-d Studio by AutoDesk which mat be running on remote PC 505 or on computer 500). The integration of the shaded polygonal meshes of upper and lower jaw occlusal surfaces in their closed bite position and the MRI or CAT/CT Scan record of the patient's oral anatomy provides the examining medical professional with a more comprehensive record of the patient's oral anatomy thus enhancing the orthognathic and dental surgical planning process.

c. Method for Matching the Two Electronic Data Sets

Figure 22:
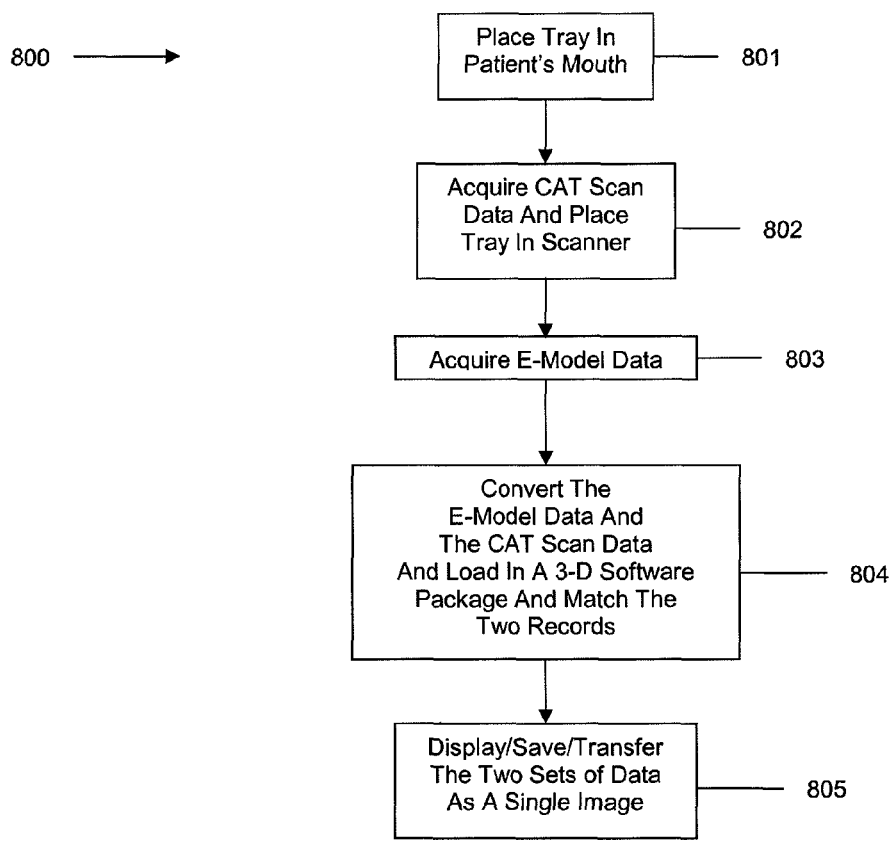
FIG. 22 is an illustration of the method steps used to practice the principles of the present invention.

FIG. 22 illustrates the method steps utilized to practice the principles of the present invention. The method is shown generally at 800.

At block 801 of FIG. 22, using the special dental impression tray, the patient that has been prescribed a MRI or CAT/T scan record of the patient's oral anatomy, inserts the special dental tray with the dental impression material applied to both sides of the special impression tray (sufficient material must be added to cover the netting material in the internal portion of the special impression tray).

At block 802, the patient keeps the special impression tray in their mouth, with their teeth in their current closed bite position, as they are undergoing the acquisition of the MRI or CAT/CT Scan record of the patient's oral anatomy. The MRI or CAT/CT Scan record of the patient's oral anatomy is then acquired and the digital file from the MRI or CAT/CT Scan device is delivered with the special impression tray to the laser scanning system that will create the digital three-dimensional dental model record of the patient's teeth and gum tissue.

At block 803, using the laser scanning system as described above, the special impression tray is scanned such that both upper and lower teeth impression surfaces are accurately three-dimensionally mapped along with the titanium markers. In this manner, an E-MODEL data set is generated.

At block 804, the two digital medical records, the digital three-dimensional dental model record of the patient's teeth and gum tissue and the digital file from the MRI or CAT/CT Scan device, are matched in the same software program using the titanium markers that are represented in both digital files. The titanium markers provide the mathematical means for accurately integrating the patient's teeth and gum tissue surface information with the bone structure, nerve, and facial soft tissue information acquired from the MRI or CAT/CT Scan device. Any of a number of commercial software packages can be used for viewing the two digital files in a three-dimensional format and the same software packages often possess the feature for matching selected three-dimensional objects.

At block 805, with the two digital files in a common three-dimensional file format and being viewed in a common three-dimensional software package. The oral surgeon now has a more accurate medical file of the patient's cranio-facial anatomy from which to plan the potential surgery process. An example of such an image is shown in FIG. 24 at 810.

d. Optional Plastic Splint Devices

The integration of the shaded polygonal meshes of upper and lower jaw occlusal surfaces in their closed bite position and the MRI or CAT/CT Scan record of the patient's oral anatomy provides the examining medical professional with a more comprehensive record of the patient's oral anatomy and with supporting software tools for simulating surgical procedures on the computer can produce any of the following splints used in the treatment of orthotic, orthognathic, and restorative dental problems requiring surgical correction:

1. Orthotic Splint for alleviating TMJ dysfunction;
2. Orthognathic Surgical Splint for configuring dentiton into final occlusion during and after surgery; and/or
3. Dental Implant Surgical Splint for establishing surgical drill alignment in a plastic sterilizable splint that is specifically fit to the patient's existing teeth.

All of the above splints are produced by transferring the above three-dimensional computer files to any commercially available Rapid Prototyping Device.

While a particular embodiment of the invention has been described, it will be understood that by those skilled in the art that the invention is not limited by the application, embodiment or the particular devices disclosed and described herein. It will be appreciated that other devices that embody the principles of this invention and other applications therefor other than as described herein can be configured within the spirit and intent of this invention. The system described herein is provided as only one example of an embodiment that incorporates and practices the principles of this invention. Other modifications and alterations are well within the knowledge of those skilled in the art and are to be included within the broad scope of the appended claims.

What is claimed is:

1. A registration apparatus for locating reference points between two cranio-facial electronic data sets relating to a patient, comprising:
    a) a U-shaped member for placement in the mouth of the patient;
    b) a registration marker cooperatively connected to the U-shaped member;
    c) a first set of electronic data, the first set of data including position information of the registration marker, wherein the first set of electronic data is generated by a CAT scan; and
    d) a second set of electronic data, the second set of data including position information of the registration marker and generated by a light based scanner, wherein the registration marker is constructed of a material such that the spatial location of the registration means is recorded during the collection of each of the two electronic data sets, whereby the two data sets may be combined by matching the recorded location of the registration marker on the two electronic data sets.

2. The apparatus of claim 1, wherein the registration marker is titanium and the light based scanner is a laser scanner.

3. The apparatus of claim 1, wherein there are three or more physically separated objects included in the registration marker.

4. A method of combining a cranio-facial CAT scan electronic data set with an electronic data set of the teeth and surrounding soft tissue, comprising the steps of:
    a) inserting a dental impression tray including registration means into a patient's mouth;
    b) holding the impression tray in the patient's mouth during the acquisition of the CAT scan data, wherein the spatial location of the registration means is recorded by during the acquisition of the CAT scan data;
    c) scanning the impression tray with a laser scanner, wherein both upper and lower teeth impression surfaces are accurately three-dimensionally mapped along with the registration means; and
    d) combining the CAT scan data with the laser scan data by matching the registration data.

5. A registration apparatus for locating reference points between two cranio-facial electronic data sets relating to a patient, comprising:
    a) a member for placement in the patient's mouth, the member being arranged and configured to take an impression;
    b) a registration marker cooperatively connected to the member, the registration marker being constructed of a material such that the spatial location of the registration means is recorded during the collection of each of the two electronic data sets;
    c) a first set of electronic data, the first set of data including data relating to a cranio-facial feature of the patient and the position of the registration marker; and
    d) a second set of electronic data, the second set of data including data relating to a cranio-facial feature of the patient and the position of the registration marker; wherein the two data sets may be combined by matching the recorded location of the registration marker on the two electronic data sets.

6. The apparatus of claim 5, wherein the registration marker is titanium.

7. The apparatus of claim 6, wherein there are three or more objects included in the registration marker.

* * * * *